United States Patent [19]
Lantzsch et al.

[11] Patent Number: 6,150,528
[45] Date of Patent: Nov. 21, 2000

[54] METHOD FOR PRODUCING 5-AMINOMETHYL-2-CHLOROPYRIDINES

[75] Inventors: Reinhard Lantzsch, Wuppertal; Uwe Stelzer, Burscheid, both of Germany

[73] Assignee: Bayer Aktiengesellschaft, Leverkusen, Germany

[21] Appl. No.: 09/380,955

[22] PCT Filed: Mar. 2, 1998

[86] PCT No.: PCT/EP98/01163

§ 371 Date: Sep. 10, 1999

§ 102(e) Date: Sep. 10, 1999

[87] PCT Pub. No.: WO98/41504

PCT Pub. Date: Sep. 24, 1998

[30] Foreign Application Priority Data

Mar. 14, 1997 [DE] Germany .......................... 197 10 613

[51] Int. Cl.$^7$ ................................................ C07D 213/38
[52] U.S. Cl. ............................................................. 546/329
[58] Field of Search ............................................... 546/329

[56] References Cited

U.S. PATENT DOCUMENTS

| | | | |
|---|---|---|---|
| 4,678,795 | 7/1987 | Shiokawa et al. | 514/341 |
| 4,774,247 | 9/1988 | Shiokawa et al. | 514/256 |
| 4,778,896 | 10/1988 | Gallenkamp | 546/304 |
| 4,812,571 | 3/1989 | Shiokawa et al. | 546/296 |
| 5,198,549 | 3/1993 | Gunther | 546/345 |
| 5,324,841 | 6/1994 | Nishimura et al. | 546/345 |

FOREIGN PATENT DOCUMENTS 5-294932  11/1993  Japan .

*Primary Examiner*—Zinna Northington Davis
*Attorney, Agent, or Firm*—Joseph C. Gil

[57] ABSTRACT

The present invention relates to the preparation of 5-aminomethyl-2-chloropyridines by reacting a mixture of 5-chloromethyl-2-chloropyridine and 5-dichloromethyl-2-chloropyridine with substituted amines. The mixture of 5-chloromethyl-2-chloropyridine and 5-dichloromethyl-2-chloropyridine is obtained by chlorination of 5-methyl-2-chloropyridine.

1 Claim, No Drawings

METHOD FOR PRODUCING 5-AMINOMETHYL-2-CHLOROPYRIDINES

This application is a 371 of PCT/EP98/01163 filed Mar. 2, 1998.

The present invention relates to the preparation of 5-aminomethyl-2-chloropyridines by reacting a mixture of 5-chloromethyl-2-chloropyridine and 5-dichloromethyl-2-chloropyridine with substituted amines. The mixture of 5-chloromethyl-2-chloropyridine and 5-dichloromethyl-2-chloropyridine is obtained by chlorination of the 5-methyl-2-chloropyridine.

The reaction of 5-chloromethyl-2-chloropyridine with amines to give substituted 5-aminomethyl-2-chloropyridines is known. However, for this purpose, it is necessary to prepare the starting material 5-chloromethyl-2-chloropyridine in high purity. To this end, 5-methyl-2-chloropyridine is chlorinated. In order to prevent the formation of more highly chlorinated pyridines such as 5-dichloro- or 5-trichloromethyl-pyridines, the chlorination must be terminated at low conversions. The resulting product then contains high amounts of starting material which must be removed and returned to the halogenation. Carrying out this reaction in industry is expensive.

It has become known that 5-aminomethyl-2-chloropyridines are also obtained when 5-trichloromethyl-2-chloromethylpyridine is reacted with amines under reducing conditions. However, this produces large amounts of salt-containing wastewater—3 mol of chloride are produced per mole of aminomethylpyridine, which must be disposed of, which is costly. In addition, the yields of this process are not always satisfactory.

It has now been found that 5-aminomethyl-2-chloropyridines of the formula (I)

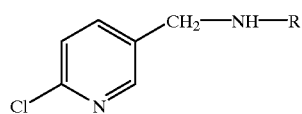

(I)

in which

R is hydrogen or optionally substituted $C_1$–$C_4$-alkyl are obtained when, in a first stage, 5-methyl-2-chloropyridine in the form of its salt is chlorinated using inorganic acids optionally in the presence of a diluent at temperatures between 50 and 150° C., preferably in the presence of a free-radical former until the content of 5-methyl-2-chloropyridine is <about 3%, and then, optionally after the diluent has been removed, in a second stage, the resulting reaction mixture is reacted with amine of the formula (II)

 R—NH$_2$ (II)

in which

R is hydrogen or optionally substituted $C_1$–$C_4$-alkyl under reducing conditions.

The novel process avoids the complex selective chlorination of 5-ethyl-2-chloropyridine and the equally complex purification and separation procedures. The novel process avoids the formation of large amounts of salt-containing wastewater.

It was not to be expected that the reaction of the reaction mixture of 5-chloromethyl and 5-dichloromethyl-2-chloropyridine with amine produces the desired 5-amino-2-chloropyridine in good yields and high purity. It was completely surprising that the reaction using the mixture produces even better yields than when the corresponding pure trichloromethyl- or dichloromethylpyridines are used.

Furthermore, it was surprising that under reducing conditions, cleavage of the 2-chlorine atom on the pyridine ring is suppresssed.

In formula (I), R is preferably hydrogen or $C_1$–$C_4$-alkyl, which is optionally substituted by OH, NH$_2$ or —NHR.

R is, in particular, methyl, ethyl, n-, iso-propyl, n-butyl, which are optionally substituted by OH, NH$_2$ or —NH—($C_1$–$C_4$)-alkyl.

R is particularly preferably ethyl or n-propyl which are substituted by OH, NH$_2$ or —NHCH$_3$.

In the first stage, the salts of 5-methyl-2-chloropyridine used are preferably hydrochloride or sulphate. Particular preference is given to the hydrochloride.

The chlorination is carried out either in the presence of diluents or without diluents in the melt. Diluents which may be mentioned are chlorinated hydrocarbons such as, for example, tetrachloromethane, or else acetonitrile or water.

The chlorination is carried out at about 50–150° C., preferably at 70–120° C.

The chlorination can preferably be carried out in the presence of a free-radical former, such as azoisobutyronitrile or a peroxide such as benzoyl peroxide.

The course of the chlorination is continually monitored, for example by gas chromatography. The chlorination is terminated when the content of 5-methyl-2-chloropyridine has dropped below about 3%.

At this point, a mixture of about from 1 to 95% of 5-chloromethyl-2-chloropyridine and about 5–99% of 5-dichloromethyl-2-chloropyridine has formed. This mixture is used in the second stage either as it is or following removal of the diluent used in the chlorination.

In the second stage, from about 2 to 30 equivalents of amine of the formula II are used per equivalent of pyridine compound to be reacted.

Preference is given to using from 3 to 15 equivalents of amine.

The second stage of the novel reaction can be carried out in the diluent used in the first stage or, following removal of the same, in another diluent. Diluents which may be mentioned are:

inert organic diluents or water.

Particular mention may be made of:

water, alcohols, hydrocarbons, halogenated hydrocarbons, ethers or mixtures of these solvents in particular with water.

Alcohols which may be mentioned are:

methanol, ethanol, isopropanol.

Hydrocarbons which may be mentioned are:

toluene, xylene.

Halogenated hydrocarbons which may be mentioned are:

chlorobenzene, dichlorobenzene.

Ethers which may be mentioned are:

diethyl ether, diisopropyl ether, methyl t-butyl ether, TAME (t-amyl methyl ether).

Particular preference is given to mixtures of water and alcohols.

The second stage of the reaction is carried out under reducing conditions. To this end, the reaction is carried out under hydrogen in the presence of Raney nickel or Raney cobalt. A hydrogen pressure of from 1 to 30 bar, preferably from 1 to 15 bar, is used.

The reaction temperature is from 20 to 50° C., preferably ambient temperature. The reaction is carried out until no more hydrogen is absorbed.

3

The reaction mixture obtained in the second stage is worked up in a customary manner, for example by filtering off the catalyst, distilling off the solvent and the amine, and purifying the resulting residue by distillation.

The examples below illustrate the subject-matter of the invention without limiting it in any way.

EXAMPLE 1

Chlorination of 2-chloro-5-methylpypridine (CMP) for the Preparation of a Mixture of 2-chloro-5-chloromethyl/dichloromethyl-pyridine (CCMP/DCMP)

94.8 g (0.6 mol) of 2-chloro-5-methyl-pyridine hydrochloride are introduced into 500 ml of tetrachloromethane and heated until boiling. Then, over the course of 5.5 hours, 62.5 g (0.88 mol) of chlorine are introduced, and simultaneously 1.8 g of azo-bis-isobutyronitrile in 300 ml of tetrachloromethane are added dropwise. This gives a clear reaction mixture.

After the mixture has been cooled, water is added and a sodium hydroxide solution is used to render it alkaline. The organic phase is separated off, washed once with water, dried and concentrated by evaporation.

This gives 103.6 g of a chlorination mixture 45% of which, according to analysis by gas chromatography, consists of CCMP and 55% of which consists of DCMP. The CMP content is <1%.

EXAMPLE 2

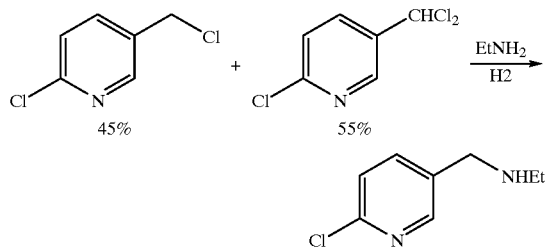

A 0.3 l autoclave is charged with 128.6 g (2 mol) of 70% strength aqueous ethylamine solution. 5 g of Raney nickel are added and the autoclave is flushed with hydrogen.

Then, at 35° C., 30 g of a chlorination mixture (45% CCMP, 55% DCCP) dissolved in 40 ml of ethanol are pumped in, while the hydrogen pressure is maintained at 9.5 bar. After 3 hours, no more hydrogen is absorbed; the autoclave is cooled and decompressed, and the catalyst is filtered off. A sodium hydroxide solution is added, and ethylamine+ethanol are distilled off.

The aqueous phase is extracted three times with toluene, and the organic phases are combined and worked up by distillation.

The toluene is distilled off to leave 26.6 g of a brown oil, which is purified by distillation.

Yield: 24.6 g 2-chloro-5-ethylaminomethylpyridine (86.3% of theory)

4

EXAMPLE 3

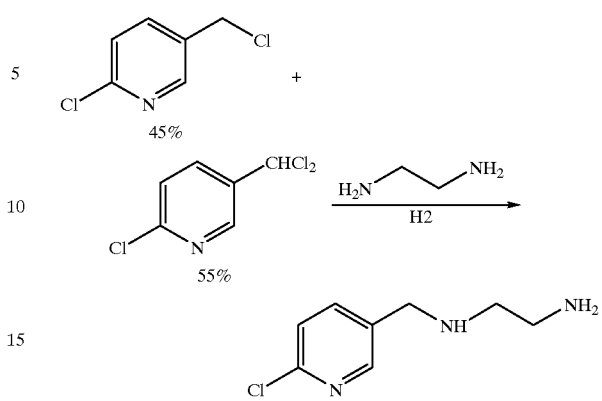

The 2 l autoclave is charged with 436.8 g (7.28 mol) of ethylenediamine, 239 g of ethanol and 10 g Raney nickel and flushed with hydrogen.

Then, at 35° C., 102.2 g of the "chlorination mixture" (45% CCMP, 55% DCCP) in 156 g of ethanol at 35° C. are pumped in, while the hydrogen pressure is maintained at between 3 and 9 bar. When no more hydrogen is absorbed, the autoclave is cooled to room temperature and decompressed, and the catalyst is filtered off. The filtrate is evaporated by concentration at 40° C. in a water-pump vacuum.

This gives 161.6 g of a clear, brown oil 49.8% of which, according to HPLC analysis with an internal standard, consists of 2-chloro-5-aminoethyl-aminomethyl-pyridine, corresponding to a yield of 76.0% of theory.

COMPARATIVE EXAMPLE A

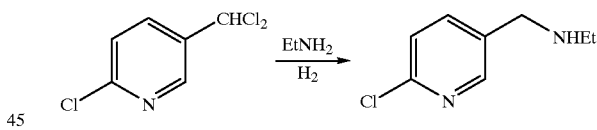

A 0.3 l autoclave is charged with 128.6 g (2.0 mol) of a 70% strength ethylamine solution; 5 g of Raney nickel are added thereto and the autoclave is flushed with hydrogen.

Then, at 35° C., 49.1 g (0.25 mol) of 5-dichloromethyl-2-chloro-pyridine dissolved in 70 ml of ethanol are pumped in, while the hydrogen pressure is maintained at 9.5 bar. When no more hydrogen is absorbed, the autoclave is cooled to room temperature and decompressed, and the catalyst is filtered off. Excess ethylamine and ethanol are distilled off.

The aqueous phase is extracted three times with toluene, and the organic phases are combined, dried and worked up by distillation.

Distilling off the toluene leaves 34.9 g of a pale red oil, which is distilled in a water-pump vacuum.

This gives 21.7 g of 2-chloro-5-ethylaminomethylpyridine (50.9% of theory) having a boiling point of 115–117° C./5 mbar.

COMPARATIVE EXAMPLE B

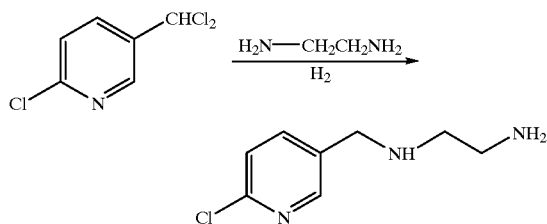

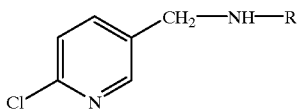

A 100 ml autoclave is charged with 42 g, 0.7 mol of ethylenediamine, 23 g of ethanol and 2.5 g of Raney nickel, and the autoclave is flushed with hydrogen. Then, at 35° C., 9.8 g (0.05 mol) of dichloromethyl-chloropyridine dissolved in 10 ml of ethanol are pumped in, while the hydrogen pressure is maintained at 3–9 bar. When no more hydrogen is absorbed, the autoclave is cooled to room temperature and decompressed, the catalyst is filtered off and the filtrate is concentrated by evaporation (water-pump vacuum, 40° C.). This gives 12.3 g of a clear, brown oil 39.8% of which, according to HPLC analysis with a internal standard, consists of 2-chloro-5-aminoethyl-aminomethyl-pyridine, corresponding to a yield of 52.7% of theory.

What is claimed is:

1. A process for the preparation of a 5-aminomethyl-2-chloropyridines of the formula (I)

wherein

R is hydrogen or optionally substituted $C_1$–$C_4$-alkyl, comprising chlorinating in a first stage, 5-methyl-2-chloropyridine in the form of its salt using inorganic acids optionally in the presence of a diluent at temperatures between 50 and 150° C., in the presence of a free-radical former until the content of 5-methyl-2-chloropyridine is <about 3%, and then, optionally after the diluent has been removed, in a second stage reacting, the resulting reaction mixture with amine of the formula (II)

$$R\text{—}NH_2 \qquad (II)$$

wherein

R is hydrogen or optionally substituted $C_1$–$C_4$-alkyl under reducing conditions.

* * * * *